(12) United States Patent
Vyas et al.

(10) Patent No.: US 10,206,925 B2
(45) Date of Patent: Feb. 19, 2019

(54) TOPICAL FORMULATIONS OF PDE-4 INHIBITORS AND THEIR METHODS OF USE

(71) Applicants: Dermavant Sciences GmbH, Basel (CH); Eisai R&D Management Co., Ltd., Tokyo (JP)

(72) Inventors: Ambrish Vyas, Cary, NC (US); Seiji Takemoto, Gifu (JP); Yoshihiro Akimoto, Gifu (JP)

(73) Assignees: Eisai R&D Management Co, Ltd., Tokyo (JP); Dermavant Sciences GmbH, Basel (CH)

( * ) Notice: Subject to any disclaimer, the term of this patent is extended or adjusted under 35 U.S.C. 154(b) by 0 days.

(21) Appl. No.: 15/616,405

(22) Filed: Jun. 7, 2017

(65) Prior Publication Data

US 2017/0348311 A1   Dec. 7, 2017

Related U.S. Application Data

(60) Provisional application No. 62/488,495, filed on Apr. 21, 2017, provisional application No. 62/449,753, filed on Jan. 24, 2017, provisional application No. 62/347,006, filed on Jun. 7, 2016.

(51) Int. Cl.
| | | |
|---|---|---|
| *A61K 31/517* | (2006.01) | |
| *A61K 47/06* | (2006.01) | |
| *A61K 47/10* | (2017.01) | |
| *A61K 47/14* | (2017.01) | |
| *A61K 9/00* | (2006.01) | |

(52) U.S. Cl.
CPC .......... *A61K 31/517* (2013.01); *A61K 9/0014* (2013.01); *A61K 47/06* (2013.01); *A61K 47/10* (2013.01); *A61K 47/14* (2013.01)

(58) Field of Classification Search
CPC .... A61K 31/517; A61K 9/0014; A61K 47/06; A61K 47/10; A61K 47/14
See application file for complete search history.

(56) References Cited

U.S. PATENT DOCUMENTS 7,939,540 B2   5/2011   Miyazaki et al.
8,530,654 B2   9/2013   Yamamoto et al.
2011/0021545 A1   1/2011   Kimura et al.

FOREIGN PATENT DOCUMENTS

WO   199937622 A1   7/1999
WO   2006085127 A1   8/2006

OTHER PUBLICATIONS

Andoh et al., Antipruritic Mechanisms of Topical E6005, a Phosphodiesterase 4 Inhibitor: Inhibition of Responses to Proteinase-activated Receptor 2 Stimulation Mediated by Increase in Intracellular Cyclic AMP (2014) J. Dermatol. Science 76:206-2
Andoh et al Topical E6005, a Novel Phosphodiesterase 4 Inhibitor, Attenuates Spontaneous Itch-related Responses in Mice with Chronic Atopy-like Dermatitis (2014) Experimental Dermatoloty 23:345-368.
Gao et al., Establishment of allergic dermatitis in NC/Nga mice as a model for severe atopic dermatitis, Biol. Pharm. Bull. Sep. 2004; 27(9): 1376-81.
Ishii et al., Antipruritic Effect of the Topical Phosphodiesterase 4 Inhibitor E6005 Ameliorates Skin Lesions in a Mouse Atopic Dermatitis Mode (Jul. 2013) J. Pharmacol. Exp. Ther. 346:105-112.
Ishii et al., Effect of the Phosphodiesterase 4 Inhibitor E6005 on Nerve Growth Factor Elevation in Irritated Skin of NC/Nga Mice (2014) J. Dermatol. Science 76:255-271.
Niemoto et al., Effect of Topical Phosphodiesterase 4 Inhibitor E6005 on Japanese Children with Atopic Dermatitis: Results from a Randomized, Vehicle-controlled Exploratory Trial (2015) J. Dermatol. 42:1-7.
Suto et al., NC/Nga mice: a mouse model for atopic dermatitis; Int Arch Allergy Immunol. 1999; 120 Suppl 1:70-5.
Wakita et al., A Putative Antipruritic Mechanism of the Phosphodiesterase-4 Inhibitor E6005 by Attenuating Capsaicin-induced Depolarization of C-fibre Nerves (2015) Experimental Dermatology 24:215-239.
International Search Report and Written Opinion for PCT/US17/36381 dated Sep. 1, 2017.

*Primary Examiner* — Sahar Javanmard
(74) *Attorney, Agent, or Firm* — Pepper Hamilton LLP

(57) ABSTRACT

Embodiments herein are directed to topical formulations of a compound represented by the formula (I), salt, metabolite, prodrug, or hydrate thereof along with a solvent, and a base. The compound is a PDE4 inhibitor and the topical formulations may be used to treat dermatological conditions such as, but not limited to, atopic dermatitis, seborrheic dermatitis, alopecia, contact dermatitis, psoriasis, urticaria, eczema, burns, sunburn, pancreatitis, hepatitis, lichen planus, scleritis, scleroderma, dermatomyositis, itching associated with any of the preceding conditions or a combination thereof.

40 Claims, 8 Drawing Sheets

TOPICAL FORMULATIONS OF PDE-4 INHIBITORS AND THEIR METHODS OF USE

CROSS-REFERENCES TO RELATED APPLICATIONS

This application claims priority to and benefit of U.S. Provisional Application No. 62/347,006 filed Jun. 7, 2016, U.S. Provisional Application No. 62/449,753 filed Jan. 24, 2017, and U.S. Provisional Application No. 62/488,495 filed Apr. 21, 2017, the entire contents of which are hereby incorporated by reference.

SUMMARY

Embodiments herein are directed to a topical formulation, comprising a compound represented by the formula (I), salt thereof, or hydrate thereof, a solvent, and a base:

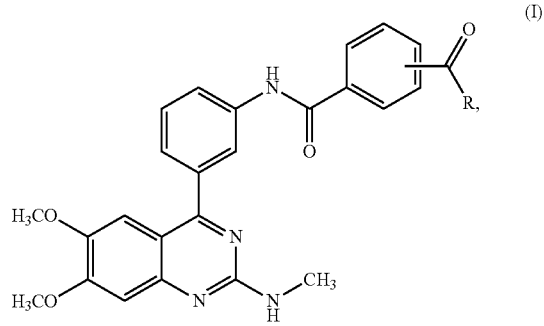

(I)

wherein R represents hydroxyl, C1-6 alkoxy optionally substituted with C1-6 alkoxy, or amino optionally substituted with C1-6 alkyl, wherein the topical formulation comprises greater than about 30% by weight of a solvent. In some embodiments, the topical formulation comprises less than about 10% of the base. In some embodiments, the topical formulation further comprises an absorption enhancer, a bleeding preventing agent, water, pharmaceutically acceptable excipient, or a combination thereof. In some embodiments, the topical formulation further comprises two or more bleeding preventing agents. In some embodiments, the total amount of the bleeding preventing agents is greater than about 40%. In some embodiments, the topical formulation comprises about 5% to about 20% by weight of an absorption enhancer. In some embodiments, the sum of the solvent and absorption enhancer is 35 to 70% by weight.

In some embodiments, the compound represented by the formula (I) is methyl N-[3-(6,7-dimethoxy-2-methylaminoquinazolin-4-yl)phenyl]terephthalamic acid (RVT-501) having the structure:

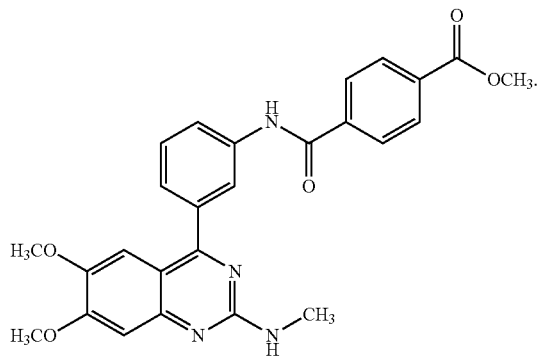

In some embodiments, the base is selected from the group consisting of petrolatum, paraffin, liquid paraffin, microcrystalline wax, carnauba wax, white beeswax, and a combination thereof.

In some embodiments, the solvent is selected from the group consisting of polyethylene glycol having an average molecular weight of 200 to 600, dipropylene glycol, benzyl alcohol, polyoxyethylene sorbitan fatty acid ester, diethylene glycol monoethyl ether, propylene glycol, polyoxyethylene oleyl ether, polyoxyethylene octyl phenyl ether, polyoxyethylene lauryl ether, polyoxyethylene castor oil, oleic acid, and a combination thereof.

In some embodiments, the topical formulation may further comprise an absorption enhancer. In some embodiments, the absorption enhancer is selected from the group consisting of isopropyl myristate, ethyl myristate, octyldodecyl myristate, isopropyl palmitate, isostearyl palmitate, isopropyl isostearate, butyl stearate, ethyl oleate, decyl oleate, diisopropyl sebacate, diethyl sebacate, diisopropyl adipate, diethyl adipate, diethyl phthalate, and a combination thereof.

In some embodiments, the topical formulation may further comprise a bleeding preventing agent. In some embodiments, the bleeding preventing agent is selected from the group consisting of polyethylene glycol having an average molecular weight of 1000 to 50000, polyoxyethylene hydrogenated castor oil, stearic acid, oleic acid, sorbitan monostearate, sorbitan monooleate, sorbitan sesquioleate, sorbitan trioleate, glycerol esters of fatty acids, and a combination thereof.

In some embodiments, the glycerol esters of fatty acids is selected from the group consisting of Geleol™ (glycerol monostearate 40-55; monoglycerides and diglycerides NF), glycerol monostearate, diglyceryl isostearate, and hexaglyceryl polyricinoleate. In some embodiments, two or more bleeding preventing agents may be used. In some embodiments, the bleeding preventing agent is polyethylene glycol having an average molecular weight of 1000 to 50000 and glycerol esters of fatty acids. In some embodiments, the glycerol esters of fatty acids is glycerol monostearate. In some embodiments, the glycerol esters of fatty acids is Geleol™ Without wishing to be bound, it is believed that using Geleol™, which includes glyceryl distearate as well as glycerol monostearate, in the topical formulation could make for a better emulsifier.

Some embodiments herein are directed to a method for preventing bleeding of liquid ingredients in a topical formulation, comprising mixing polyethylene glycol having an average molecular weight of 1000 to 50000 and glycerol esters of fatty acids in a topical formulation according to embodiments herein.

DESCRIPTION OF DRAWINGS

For a fuller understanding of the nature and advantages of the present invention, reference should be had to the following detailed description taken in connection with the accompanying drawings, in which.

DETAILED DESCRIPTION

Figure 1:
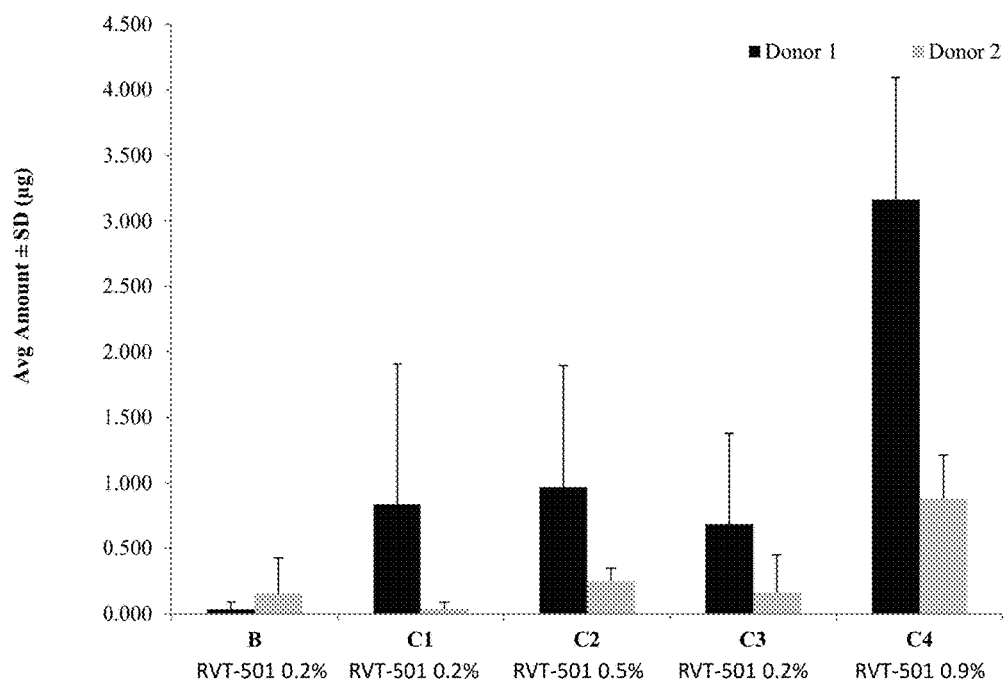
FIG. 1 illustrates the mean amount (μg) of a compound of formula (I) of embodiments herein collected from the stratum corneum of each donor 24 hours after application of the topical formulation of embodiments herein.

Before the present compositions and methods are described, it is to be understood that this invention is not limited to the particular processes, formulations, compositions, or methodologies described, as these may vary. It is also to be understood that the terminology used in the description is for the purpose of describing the particular versions or embodiments only, and is not intended to limit the scope of the present invention which will be limited only by the appended claims. Unless defined otherwise, all technical and scientific terms used herein have the same meanings as commonly understood by one of ordinary skill in the art. Although any methods and materials similar or equivalent to those described herein can be used in the practice or testing of embodiments of the present invention, the preferred methods, devices, and materials are now described. All publications mentioned herein are incorporated by reference in their entirety. Nothing herein is to be construed as an admission that the invention is not entitled to antedate such disclosure by virtue of prior invention.

Phosphodiesterase 4 inhibitor (hereinafter abbreviated as PDE4 inhibitor) is a drug that suppresses the action of the enzyme phosphodiesterase, which degrades cyclic AMP (hereinafter abbreviated as cAMP) and, as a result, has effects of increasing intracellular cAMP concentrations to relax smooth muscle and suppressing activation of inflammatory cells. Some PDE4 inhibitors are poorly absorbed into the skin when used as a topical product. Therefore, to improve the absorption property, it may occasionally be necessary to include a liquid ingredient such as a large quantity of solvent to dissolve the compound, or an absorption enhancer in the formulation. However, this may cause phase separation and bleeding of the liquid components from the formulation. Accordingly, a goal of this disclosure is to provide a topical formulation which allows high absorption of a PDE4 inhibitor and does not result in bleeding of the component.

Compound of Formula (I)

Embodiments herein disclose a compound represented by formula (I), salt thereof, or hydrate thereof.

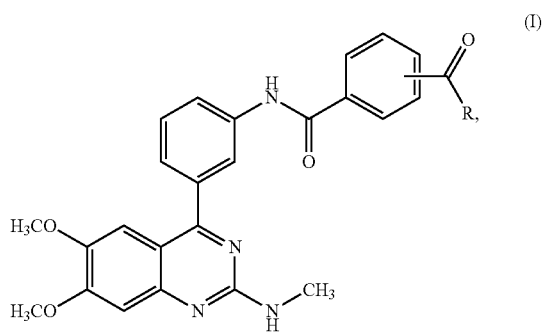

wherein R represents hydroxyl, C1-6 alkoxy optionally substituted with C1-6 alkoxy, or amino optionally substituted with C1-6 alkyl.

Examples of the compound represented by the formula (I) include: methyl N-[3-(6,7-dimethoxy-2-methyl aminoquinazolin-4-yl)phenyl]terephthalamic acid; N-[3-(6,7-dimethoxy-2-methylaminoquinazolin-4-yl)phenyl]terephthalamic acid hydrochloride; N-[3-(6,7-dimethoxy-2-methylaminoquinazolin-4-yl)phenyl]-N',N'-dimethylterephthalamide; ethyl N-[3-(6,7-dimethoxy-2-methylaminoquinazolin-4-yl)phenyl]terephthalamic acid; N-[3-(6,7-dimethoxy-2-methylaminoquinazolin-4-yl)phenyl]-N'-methylterephthalamide; propyl N-[3-(6,7-dimethoxy-2-methyl aminoquinazolin-4-yl)phenyl]terephthalamic acid; isopropyl N-[3-(6,7-dimethoxy-2-methyl aminoquinazolin-4-yl)phenyl]terephthalamic acid; N-[3-(6,7-dimethoxy-2-methylaminoquinazolin-4-yl]-N'-ethylterephthalamide; N-[3-(6,7-dimethoxy-2-methylaminoquinazolin-4-yl)phenyl]-N'-propylterephthalamide; N-[3-(6,7-dimethoxy-2-methylaminoquinazolin-4-yl)phenyl]-N'-isopropylterephthalamide; methyl N-[3-(6,7-dimethoxy-2-methylaminoquinazolin-4-yl)phenyl]isophthalic acid; N-[3-(6,7-dimethoxy-2-methylaminoquinazolin-4-yl)phenyl] isophthalic acid; ethyl N-[3-(6,7-dimethoxy-2-methylaminoquinazolin-4-yl)phenyl]isophthalic acid; propyl N-[3-(6,7-dimethoxy-2-methylaminoquinazolin-4-yl)phenyl]isophthalic acid; isopropyl N-[3-(6,7-dimethoxy-2-methylaminoquinazolin-4-yl)phenyl]isophthalic acid; N-[3-(6,7-dimethoxy-2-methylaminoquinazolin-4-yl)phenyl]-N'-methylisophthalamide; N-[3-(6,7-dimethoxy-2-methylaminoquinazolin-4-yl)phenyl]-N'-ethylisophthalamide; N-[3-(6,7-dimethoxy-2-methylaminoquinazolin-4-yl)phenyl]-N'-propylisophthalamide; N-[3-(6,7-dimethoxy-2-methylaminoquinazolin-4-yl)phenyl]-N'-isopropylisophthalamide; N-[3-(6,7-dimethoxy-2-methylaminoquinazolin-4-yl)phenyl]terephthalamic acid 2-methoxyethyl ester; and N-[3-(6,7-dimethoxy-2-methyl-aminoquinazolin-4-yl)phenyl]isophthalamic acid 2-methoxyethyl ester. In some embodiments, the compound represented by the formula (I) is methyl N-[3-(6,7-dimethoxy-2-methylaminoquinazolin-4-yl)phenyl]terephthalamic acid (RVT-501) having the structure:

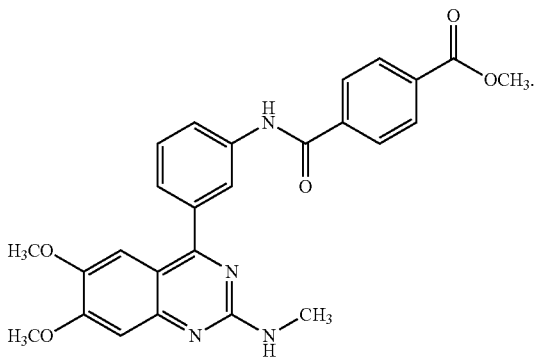 [SMILES: CNc1nc(-c2cccc(NC(=O)c3ccc(C(=O)OC)cc3)c2)c2cc(OC)c(OC)cc2n1]

The compound and methods of making such compound are further described in U.S. Pat. Nos. 7,939,540 and 8,530,654, which are each hereby incorporated by reference in its entirety.

Optical Isomers—Diastereomers—Geometric Isomers—Tautomers. Compounds described herein may contain an asymmetric center and may thus exist as enantiomers. Where the compounds according to the invention possess two or more asymmetric centers, they may additionally exist as diastereomers. Embodiments herein include all such possible stereoisomers as substantially pure resolved enantiomers, racemic mixtures thereof, as well as mixtures of diastereomers. The formulas are shown without a definitive stereochemistry at certain positions. Embodiments herein include all stereoisomers of such formulas and pharmaceutically acceptable salts thereof. Diastereoisomeric pairs of enantiomers may be separated by, for example, fractional crystallization from a suitable solvent, and the pair of enantiomers thus obtained may be separated into individual stereoisomers by conventional means, for example by the use of an optically active acid or base as a resolving agent or on a chiral HPLC column. Further, any enantiomer or diastereomer of a compound of the general formula may be obtained by stereospecific synthesis using optically pure starting materials or reagents of known configuration. Embodiments described herein include all isomers of the compound of formula (I) disclosed herein, such as a geometric isomer, an optical isomer, a stereoisomer, or a tautomer, and an isomeric mixture. Embodiments herein include both the racemic form and the optically active form. Embodiments further include a single crystal form or a mixture thereof. Moreover, embodiments herein also include an amorphous form, an anhydrate, and a hydrate form of the compound. Furthermore, embodiments herein also include metabolites, salts, hydrates, and pro-drugs of the compounds disclosed herein.

The term "C1-6 alkyl" is used in the present specification to mean a linear or branched-chain alkyl group containing 1 to 6 carbon atoms. Specific examples of $C_{1-6}$ alkyl may include methyl, ethyl, 1-propyl (n-propyl), 2-propyl (i-propyl), 2-methyl-1-propyl (i-butyl), 2-methyl-2-propyl (t-butyl), 1-butyl (n-butyl), 2-butyl (s-butyl), 1-pentyl, 2-pentyl, 3-pentyl, 2-methyl-1-butyl, 3-methyl-1-butyl, 2-methyl-2-butyl, 3-methyl-2-butyl, 2,2,-dimethyl-1-propyl, 1-hexyl, 2-hexyl, 3-hexyl, 2-methyl-1-pentyl, 3-methyl-1-pentyl, 4-methyl-1-pentyl, 2-methyl-2-pentyl, 3-methyl-2-pentyl, 4-methyl-2-pentyl, 2-methyl-3-pentyl, 3-methyl-3-pentyl, 2,3-dimethyl-1-butyl, 3,3-dimethyl-1-butyl, 2,2-dimethyl-1-butyl, 2-ethyl-1-butyl, 3,3-dimethyl-2-butyl, and 2,3-dimethyl-2-butyl. Embodiments may include $C_{1-3}$ alkyl such as methyl, ethyl, 1-propyl (n-propyl), 2-propyl (i-propyl), 2-methyl-1-propyl (i-butyl), 2-methyl-2-propyl (t-butyl), 1-butyl (n-butyl), or 2-butyl (s-butyl). Some embodiments may include methyl and ethyl.

The term "$C_{1-6}$ alkoxy" is used in the present specification to mean an oxy group to which the above defined "$C_{1-6}$ alkyl" binds. Specific examples of $C_{1-6}$ alkoxy may include methoxy, ethoxy, 1-propoxy, 2-propoxy, 2-methyl-1-propoxy, 2-methyl-2-propoxy, 1-butoxy, 2-butoxy, 1-pentoxy, 2-pentyloxy, 3-pentyloxy, 2-methyl-1-butoxy, 3-methyl-1-butoxy, 2-methyl-2-butoxy, 3-methyl-2-butoxy, 2,2-dimethyl-1-propoxy, 1-hexyloxy, 2-hexyloxy, 3-hexyloxy, 2-methyl-1-pentoxy, 3-methyl-1-pentyloxy, 4-methyl-1-pentoxy, 2-methyl-2-pentoxy, 3-methyl-2-pentoxy, 4-methyl-2-pentoxy, 2-methyl-3-pentyloxy, 3-methyl-3-pentyloxy, 2,3-dimethyl-1-butoxy, 3,3-dimethyl-1-butoxy, 2,2-dimethyl-1-butoxy, 2-ethyl-1-butoxy, 3,3-dimethyl-2-butoxy, 2,3-dimethyl-2-butoxy and the like. Some embodiments may include C1-3 alkoxy such as methoxy, ethoxy, 1-propoxy, and 2-propoxy. In some embodiments, the C1-3 alkoxy is methoxy. In addition, examples of "C1-6 alkoxy optionally substituted with C1-6 alkoxy" in the definitions of R may include methoxymethoxy, ethoxymethoxy, methoxyethoxy, and ethoxyethoxy.

Examples of "amino optionally substituted with C1-6 alkyl" in the present specification may include amino, mono-C1-6 alkylamino that is substituted with the aforementioned C1-6 alkyl (for example, methylamino, ethylamino, t-butylamino, etc.), di-C1-6 alkylamino (for example, dimethylamino, diethylamino, methylethylamino, etc.) and the like.

Some embodiments may include amino, mono-C1-3 alkylamino, and di-C1-3 alkylamino. In some embodiments, the amino optionally substituted with C1-6 alkyl may include amino and monomethylamino.

In some embodiments, a salt of compounds described herein may include an inorganic acid salt, an organic acid salt, an inorganic basic salt, an organic basic salt, an acidic or basic amino acid salt or the like. In some embodiments, the inorganic acid salt may include hydrochloride, hydrobromide, sulfate, nitrate, phosphate or the like. In some embodiments, the salt may be selected from a hydrochloride, hydrobromide, sulfate, or phosphate. In some embodiments, the organic acid salt may include acetate, succinate, fumarate, maleate, tartrate, citrate, lactate, stearate, benzoate, methanesulfonate, ethanesulfonate, p-toluenesulfonate, or benzenesulfonate. In some embodiments, the salt may be methanesulfonate or p-toluenesulfonate.

In some embodiments, the inorganic basic salt may include: alkaline metal salts such as a sodium salt or a potassium salt; alkaline-earth metal salts such as a calcium salt or a magnesium salt; aluminum salts; ammonium salts, or the like. In some embodiments, the organic basic salt may include a diethylamine salt, a diethanolamine salt, a meglumine salt, an N,N'-dibenzylethylenediamine salt, or the like.

In some embodiments, the acidic amino acid salt may include aspartate and glutamate. In some embodiments, the basic amino acid salt may include an arginine salt, a lysine salt, an ornithine salt or the like.

Method of Making Compound of Formula (I)

The compound represented by the formula (I) can be produced, for example, by the method described below.

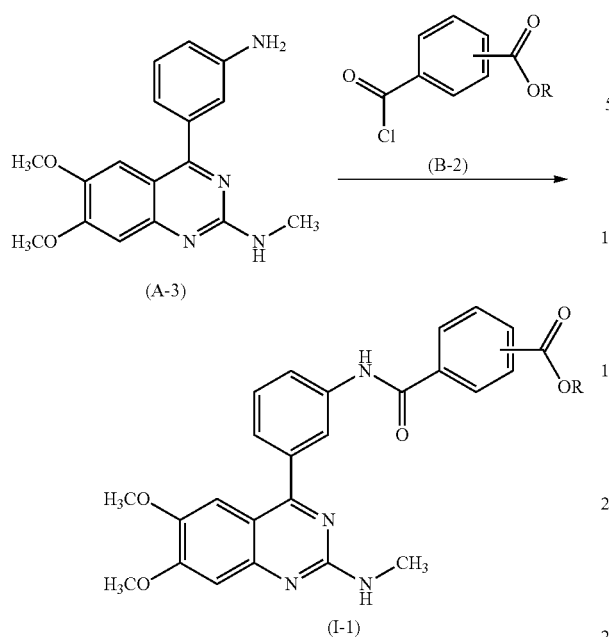

(A-3)

(I-1)

wherein R1 represents C1-6 alkyl.

In some embodiments, the method of making a compound of formula (I), the method comprising reacting a compound (A-3) with a compound (B-2) that is acid chloride in an inert solvent in the presence or absence of a base, so as to produce the compound (I-1) of embodiments herein.

A compound (A-3) can be produced by production example 7 in WO 99/37622. A compound (B-2), a known compound, a commercially available compound, or a compound that can easily be produced from a commercially available compound by a method that is generally carried out by those skilled in the art, can be used. Examples of compound (B-2) may include 4-chlorocarbonyl benzoic acid methyl ester and the like. The compound (B-2) can be used in an amount of 1 to 10 times, and preferably 1 to 2 times the molar equivalent of the compound (A-3).

In some embodiments, the solvent may include: aromatic hydrocarbons such as toluene, benzene, xylene and the like; ethers such as diethyl ether, tetrahydrofuran, dimethoxyethane, dioxane and the like; halogenated hydrocarbons such as dichloromethane, chloroform, 1,2-dichloroethane, or carbon tetrachloride; organic bases such as pyridine, 2-, 3- or 4-picoline and the like; water; or a combination thereof. In some embodiments, the solvent may include tetrahydrofuran or pyridine. In some embodiments, the reaction solvent may be polyethylene glycol.

In some embodiments, the reaction base may include: inorganic bases such as sodium carbonate, potassium carbonate, sodium hydrogencarbonate, potassium hydrogencarbonate, cesium carbonate and the like; and organic bases such as pyridine, triethylamine and the like. A preferred example is pyridine. In some embodiments, the reaction base may be used in an amount of 1 to 10 times, and preferably 1 to 4 times the molar equivalent of the compound (A-3). The reaction temperature depends on the reaction solvent and the reagent used. In some embodiments, the reaction temperature is generally between about −30° C. and about 180° C., and preferably between about 0° C. and about 100° C. The reaction time depends on the reaction solvent used and the reaction temperature. In some embodiments, the reaction time is between about 0.5 and about 200 hours. In some embodiments, the reaction time is between about 1 and about 100 hours.

In some embodiments, the method of making a compound represented by the formula (I) comprises hydrolyzing and esterifying or amidating the compound (I-1) if necessary. In some embodiments, when the compound represented by the formula (I) is obtained in a free form, such a free form can be converted to a salt or hydrate according to common methods. Furthermore, in some embodiments, when the compound represented by the formula (I) is obtained in a form of a salt or hydrate, these compounds can be converted to a free form according to common methods.

Topical Formulations

Embodiments herein are directed to a topical formulation, comprising a compound represented by the formula (I), a salt thereof, a derivative thereof, or hydrate thereof, a solvent and a base:

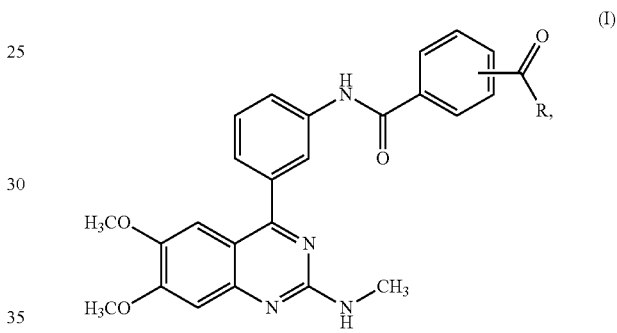

(I)

wherein R represents hydroxyl, C1-6 alkoxy optionally substituted with C1-6 alkoxy, or amino optionally substituted with C1-6 alkyl, wherein the topical formulation comprises greater than about 30% by weight of a solvent. In some embodiments, the topical formulation comprises less than about 10% of the base. In some embodiments, the topical formulation comprises about 5% to about 20% by weight of an absorption enhancer. In some embodiments, the sum of the solvent and absorption enhancer is 35 to 70% by weight. In some embodiments, the topical formulation further comprises an absorption enhancer, a bleeding preventing agent, water, pharmaceutically acceptable excipient, or a combination thereof.

In some embodiments, the compound of formula (I) is a PDE4 inhibitor. However, the compound represented by the formula (I), or salt thereof or hydrate thereof may have insufficient skin absorption properties when used as a topical formulation. Exemplary advantages of the topical formulations disclosed herein are that the formulations of embodiments herein improve the absorption properties of the compound represented by the formula (I), salt, prodrug, metabolite, or hydrate thereof, while preventing the bleeding of the components from the formulation, thereby increasing stability of the formulation.

In some embodiments, the topical formulation may be an ointment preparation, a gel preparation, a cream preparation, a patch preparation, an eye ointment preparation, a suppository preparation, or the like. In some embodiments, the topical formulation is an ointment preparation.

The active ingredient in the topical formulation according to the present invention is a compound represented by formula (I), a salt thereof, an analog thereof, a derivative thereof, or hydrate thereof:

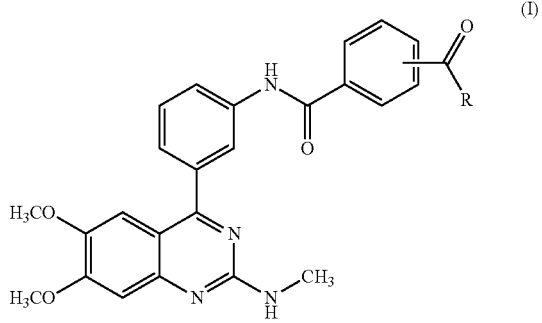

(I)

wherein R represents hydroxyl, C1-6 alkoxy optionally substituted with C1-6 alkoxy, or amino optionally substituted with C1-6 alkyl. In some embodiments, the active ingredient is methyl N-[3-(6,7-dimethoxy-2-methyl aminoquinazolin-4-yl)phenyl]terephthalamic acid (RVT-501):

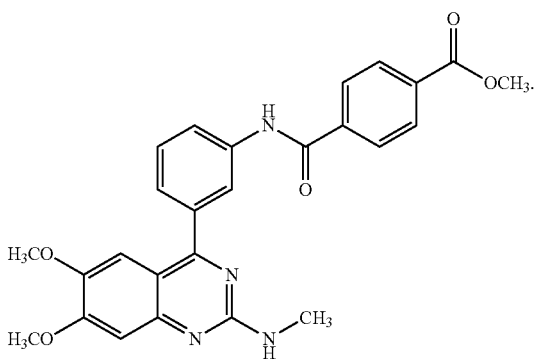 [SMILES: CNc1nc(-c2cccc(NC(=O)c3ccc(C(=O)OC)cc3)c2)c2cc(OC)c(OC)cc2n1]

Some embodiments are directed to a topical formulation comprising a solvent and a base in addition to an active ingredient. It is believed that when a topical product is formulated by mixing an active ingredient and a base, skin absorption properties may become insufficient. The skin absorbability of the active ingredient in the topical formulation of the present invention may be improved by adding a solvent.

Any solvent commonly used for a topical formulation may be used, including, but not limited to, polyethylene glycol having an average molecular weight of 200 to 600, dipropylene glycol, benzyl alcohol, polyoxyethylene sorbitan fatty acid ester, diethylene glycol monoethyl ether, propylene glycol, polyoxyethylene oleyl ether, polyoxyethylene octyl phenyl ether, polyoxyethylene lauryl ether, polyoxyethylene castor oil, oleic acid or a combination thereof. In some embodiments, the solvent is polyethylene glycol having an average molecular weight of 200 to 600.

As used herein, the term "methyl N-[3-(6,7-dimethoxy-2-methylaminoquinazolin-4-yl)phenyl]terephthalamic acid" or "RVT-501" shall also refer to alternative names of the compound, including N-[3-(6,7-dimethoxy-2-methylaminoquinazolin-4-yl)phenyl]terephthalamic methyl ester, methyl 4-[(3-[6,7-dimethoxy-2-(methylamino)quinazolin-4-yl]phenyl)carbamoyl]benzoate, and methyl 4-[({3-[6,7-dimethoxy-2-(methylamino)quinazolin-4-yl]phenyl}amino)carbonyl]benzoate.

As used herein, the term "polyethylene glycol" refers to a polymer containing ethylene glycol monomer units of formula —O—$CH_2$—$CH_2$—. Suitable polyethylene glycols may have a free hydroxyl group at each end of the polymer molecule, or may have one or more hydroxyl groups etherified with a lower alkyl, e.g., a methyl group. Also suitable are derivatives of polyethylene glycols having esterifiable carboxy groups. The number following the dash in the name refers to the average molecular weight of the polymer. In some embodiments, the average molecular weight of the polyethylene glycol having an average molecular weight of 200 to 600 is from about 200 to about 600. In some embodiments, the average molecular weight of the polyethylene glycol is about 400. Suitable polyethylene glycols include, but are not limited to polyethylene glycol-200, polyethylene glycol-300, polyethylene glycol-400, and polyethylene glycol-600. In some embodiments, the polyethylene glycol is polyethylene glycol-400. Suitable polyethylene glycols include, but are not limited to the Carbowax™ and Carbowax™ Sentry series (available from Dow), the Lipoxol™ series (available from Brenntag), the Lutrol™ series (available from BASF), and the Pluriol™ series (available from BASF).

As used herein, polyethylene glycol having an average molecular weight of 200 to 600 refers to polyethylene glycol having an average molecular weight of about 200 to about 600 as a result of average molecular weight testing. In some embodiments, the average molecular weight of the polyethylene glycol having an average molecular weight of 200 to 600 is about 200 to about 500, about 200 to about 400, about 300 to about 600, about 300 to about 500, about 300 to about 400, or a value within any of these ranges. In some embodiments, the solvent is a polyethylene glycol 400 having an average molecular weight of 380 to 420 as a result of average molecular weight testing.

In some embodiments, the base may be any base commonly used in a topical formulation. In some embodiments, the base may be an oleaginous base, including, but not limited to, petrolatum, squalane, paraffin, liquid paraffin, microcrystalline wax, carnauba wax, white beeswax and the like. In some embodiments, the base is petrolatum. As used herein, petrolatum means a mixture of semi solid saturated hydrocarbons typically obtained from petroleum. In some embodiments, petrolatum is white petrolatum, mineral oil, petroleum jelly, yellow petrolatum, amber petrolatum, vasoliments, cosmoline, saxoline, stanoline, vasiline, cold tar, or a combination thereof. In some embodiments, the base is white petrolatum. In some embodiments, the base is U.S. Pharmacopoeia (USP) white petrolatum.

In some embodiments, the topical formulation further comprises an absorption enhancer and/or bleeding preventing agent. It is believed that the skin absorbability of the active ingredient can be further improved by adding an absorption enhancer. Furthermore, it is believed that the bleeding of ingredients (in particular, a solvent and absorption enhancer) from the topical formulation of embodiments herein can be prevented by adding a bleeding preventing agent, and thus improved stability can be achieved.

In some embodiments, the topical formulation may further comprise an absorption enhancer. In some embodiments, the absorption enhancer may be any absorption enhancer commonly used in a topical formulation. In some embodiments, the absorption enhancer may be isopropyl myristate, ethyl myristate, octyldodecyl myristate, isopropyl palmitate, isostearyl palmitate, isopropyl isostearate, butyl stearate, ethyl oleate, decyl oleate, diisopropyl sebacate, diethyl sebacate, diisopropyl adipate, diethyl adipate, diethyl phthalate, or a combination thereof. In some embodiments, the absorption enhancer is isopropyl myristate.

In some embodiments, the topical formulation may further comprise a bleeding preventing agent. In some embodiments, the bleeding preventing agent may be any bleeding agent commonly used in a topical formulation. In some embodiments, the bleeding preventing agent may be polyethylene glycol having an average molecular weight of 1000 to 50000, polyoxyethylene hydrogenated castor oil, stearic acid, oleic acid, sorbitan monostearate, sorbitan monooleate, sorbitan sesquioleate, sorbitan trioleate, a glycerol ester of a fatty acid, other similar agents, or a combination thereof. In some embodiments, the glycerol ester of a fatty acid may be glycerol monostearate, diglyceryl isostearate, hexaglyceryl polyricinoleate, or other similar agents, or a combination thereof. In some embodiments, the glycerol ester of a fatty acid is glycerol monostearate. In some embodiments, the glycerol monostearate is glycerol monostearate 40-55 sold under the trademark Geleol™ Mono and Diglycerides NF. For avoidance of doubt, as used herein, the term "glycerol monostearate" may be interchangeable with "glyceryl monostearate."

In some embodiments, two or more bleeding preventing agents may be used. In some embodiments, the bleeding preventing agent is polyethylene glycol having an average molecular weight of 1000 to 50000 and glyceryl esters of fatty acids. In some embodiments, the bleeding preventing agent is polyethylene glycol having an average molecular weight of 1000 to 50000 and glycerol monostearate. In some embodiments, the bleeding preventing agent is polyethylene glycol having an average molecular weight of 1000 to 50000 and glycerol monostearate or other similar agents. It is believed that bleeding of a solvent, in particular, polyethylene glycol having an average molecular weight of 200 to 600 can be prevented by using polyethylene glycol having an average molecular weight of 1000 to 50000. Furthermore, it is believed that bleeding of an absorption enhancer, in particular, isopropyl myristate can be prevented by using glycerol monostearate or Geleol™ or other similar agents.

In some embodiments, the polyethylene glycol having a molecular weight 1000 to 50000 refers to polyethylene glycol having an average molecular weight of 1000 to 50000 as a result of average molecular weight testing. In some embodiments, the average molecular weight of the polyethylene glycol having a molecular weight of 1000 to 50000 is from about 1000 to about 50000, about 1000 to about 45000, about 1000 to about 40000, about 1000 to about 30000, about 1000 to about 25000, about 1000 to about 20000, about 1000 to about 15000, about 1000 to about 10000, about 1000 to about 5000, or a value within any of these ranges. In some embodiments, the average molecular weight of the polyethylene glycol may be 1000, 2000, 3000, 4000, 5000, 6000, 7000, 8000, 9000, 10000, 15000, 20000, 25000, 30000, 35000, 40000, 45000, 50000, or a range of any two of these values. In some embodiments, the polyethylene glycol is polyethylene glycol 4000. In some embodiments, the bleeding preventing agent is polyethylene glycol 4000 having an average molecular weight of 3600 to 4400 as a result of average molecular weight testing. In some embodiments, the polyethylene glycol-4000 is USP polyethylene glycol 4000. In some embodiments, the polyethylene glycol-4000 is Japan Pharmacopeia polyethylene glycol 4000.

In some embodiments, the topical formulation may further comprise water. In some embodiments, the topical formulation may be purified water. It is believed that degradation of an active ingredient may be suppressed by adding water.

In some embodiments, the topical formulation may further comprise a coloring agent, a flavoring agent, a preservative, an antioxidant, a stabilizer, a usability improving agent, pharmaceutically acceptable excipient, or a combination thereof.

In some embodiments, the coloring agent may be selected from iron sesquioxide, yellow iron sesquioxide, carmine, caramel, beta-carotene, titanium oxide, talc, riboflavin sodium phosphate, yellow aluminum lake, or a combination thereof. In some embodiments, the flavoring agent may be selected from cocoa powder, mentha oil, menthol, lemon oil, borneol, powdered cinnamon bark, ascorbic acid, citric acid, tartaric acid, malic acid, aspartame, potassium acesulfame, or a combination thereof.

In some embodiments, the preservative may be selected from methylparaben, propylparaben, chlorobutanol, benzyl alcohol, phenethyl alcohol, dehydroacetic acid, sorbic acid or a combination thereof.

In some embodiments, the antioxidant may include sulfite salts, ascorbic acid, tocopherol, lycopene, green tea, coffee berry, resveratrol, grape seed, niacinamide, genistein, ferulic acid, idebenone, coenzyme Q10, retinol, vitamin A, lutein, zeaxanthin, astaxanthin, alpha lipoic acid, zinc, copper, beta-carotene, or a combination thereof.

In some embodiments, the stabilizer may include ascorbic acid, edetic acid salt, erythorbic acid, tocopherol, and the like, or a combination thereof.

In some embodiments, the usability improving agent may include polyoxyethylene hydrogenated castor oil 40, polyoxyethylene hydrogenated castor oil 60, and the like, or a combination thereof.

In some embodiments, the active ingredient may be in an amount of about 0.001% to about 10% by weight. In some embodiments, the active ingredient may be in an amount of about 0.001% to about 5%, about 0.001% to about 1%, about 0.001% to about 0.5%, about 0.01% to about 0.5%, about 0.05% to about 0.5%, about 0.1% to about 1%, about 0.4% to about 0.6%, about 0.3% to about 0.7%, about 0.2% to about 0.9%, about 0.1% to about 0.5%, about 0.2% to about 0.5% by weight, or a value within any of these ranges. In some embodiments, the active ingredient may be in an amount of about 0.001%, about 0.01%, about 0.03%, about 0.05%, about 0.1%, about 0.2%, about 0.25%, about 0.3%, about 0.4%, about 0.5%, about 0.6%, about 0.7%, about 0.75%, about 0.8%, about 0.9%, about 1.0%, about 3.0%, or about 5% by weight, or a range of any two of these values.

In some embodiments, the solvent may be in an amount of greater than about 30% by weight. In some embodiments, the solvent may be in an amount of greater than about 30% by weight to about 60% by weight. In some embodiments, the solvent may be in an amount of about 35% by weight to about 60%, about 35% to about 55%, about 35% to about 50%, about 40% to about 60%, or about 40% to about 55%, about 40% to about 50% by weight. In some embodiments, the solvent may be in an amount of about 35%, about 40%, about 45%, about 50%, about 55%, about 60%, or about 65% by weight, or a range of any two of these values.

In some embodiments, the base may be in an amount of less than about 10% by weight. In some embodiments, the base may be in an amount of about 0.001% to about 10% by weight. In some embodiments, the base may be in an amount of about 0.1% by weight to about 10%, about 0.5% to about 10%, about 1% to about 10%, about 2.5% to about 10%, or about 4% to about 10%, about 0.1% by weight to about 7%, about 0.5% to about 7%, about 1% to about 7%, about 2.5% to about 7%, or about 4% to about 7%, about 4% to about 5% by weight. In some embodiments, the base may be in an amount of about 0.1%, about 1%, about 2%, about 3%, about 4%, about 4.5%, about 5%, about 6%, about 7%, about 8%, about 9%, or about 10% by weight, or a range of any two of these values. In some embodiments, the absorption enhancer may be in an amount of about 5% to about 20% by weight. In some embodiments, the absorption enhancer may be in an amount of about 5%, about 10%, about 15%, or about 20% by weight, or a range of any two of these values.

In some embodiments, the total amount of the bleeding preventing agent may be in an amount of about 20% to about 50% by weight. In some embodiments, the total amount of the bleeding preventing agent may be in an amount of greater than about 25%. In some embodiments, the total amount of the bleeding preventing agent may be in an amount of about 25% to about 50% by weight, about 25% to about 40% by weight, about 25% to about 35% by weight, or about 30% to about 50% by weight. In some embodiments, the total amount of the bleeding preventing agent may be in an amount of about 25%, about 30%, about 33%, about 35%, about 40%, about 45%, or about 50% by weight, or a range of any two of these values.

In some embodiments, the water may be in an amount of about 0.1% to about 5% by weight. In some embodiments, the water may be in an amount of about 0.3% to about 4%, about 0.3% to about 3%, about 0.5% to about 3%, or about 0.5% to about 2%. In some embodiments, the water may be in an amount of about 0.1%, about 1%, about 2%, about 3%, about 4%, about 4.5%, or about 5% by weight, or a range of any two of these values.

In some embodiments, the amount of the solvent and the absorption enhancer is about 40% to about 70% by weight. In some embodiments, the amount of the solvent and the absorption enhancer may be in an amount of about 40% to about 65% by weight, about 40% to about 60% by weight, about 40% to about 55% by weight, or about 40% to about 50% by weight. In some embodiments, the amount of the solvent and the absorption enhancer may be in an amount of about 40%, about 45%, about 50%, about 55%, about 40%, about 60%, about 65%, or about 70% by weight, or a range of any two of these values In some embodiments, the topical formulation may be selected from a formulation disclosed in Table 1 below. In some embodiments, the topical formulation may be selected from Formulation C1, Formulation C2, Formulation C3, or Formulation C4 as disclosed in Table 1 below. In some embodiments, the topical formulations used in the method of embodiments herein may comprise an effective amount of a compound represented by formula (I), a salt thereof, analog thereof, or hydrate thereof, wherein R represents hydroxyl, $C_{1-6}$ alkoxy optionally substituted with $C_{1-6}$ alkoxy, or amino optionally substituted with $C_{1-6}$ alkyl, a solvent, and a base, wherein the topical formulation comprises greater than about 30% by weight of a solvent. In some embodiments, the base is in an amount of about 0.001% to less than about 10% by weight of the topical formulation. In some embodiments, the compound represented by formula (I) is in an amount of about 0.2% to about 1% by weight of the topical formulation. In some embodiments, the compound represented by formula (I) is in an amount of about 0.2% to about 0.6% by weight of the topical formulation. In some embodiments, the compound represented by formula (I) is in an amount of about 0.5% by weight of the topical formulation.

In some embodiments, the topical formulation further comprises an absorption enhancer, a bleeding preventing agent, water, pharmaceutically acceptable excipient, or a combination thereof. In some embodiments, the bleeding preventing agent is two or more bleeding preventing agents. In some embodiments, a total amount of the bleeding preventing agent is greater than about 40% by weight of the topical formulation. In some embodiments, the absorption enhancer is in an amount of about 5% to about 20% by weight of the topical formulation. In some embodiments, the sum of the solvent and absorption enhancer is 35% to 70% by weight of the topical formulation.

In some embodiments, the compound represented by the formula (I) is methyl N-[3-(6,7-dimethoxy-2-methylamino-quinazolin-4-yl)phenyl]terephthalamic acid (RVT-501).

In some embodiments, the base is selected from the group consisting of petrolatum, paraffin, liquid paraffin, microcrystalline wax, carnauba wax, white beeswax, and a combination thereof.

In some embodiments, the solvent is selected from the group consisting of polyethylene glycol having an average molecular weight of 200 to 600, dipropylene glycol, benzyl alcohol, polyoxyethylene sorbitan fatty acid ester, diethylene glycol monoethyl ether, propylene glycol, polyoxyethylene oleyl ether, polyoxyethylene octyl phenyl ether, polyoxyethylene lauryl ether, polyoxyethylene castor oil, oleic acid, and a combination thereof.

In some embodiments, the absorption enhancer is selected from the group consisting of isopropyl myristate, ethyl myristate, octyldodecyl myristate, isopropyl palmitate, isostearyl palmitate, isopropyl isostearate, butyl stearate, ethyl oleate, decyl oleate, diisopropyl sebacate, diethyl sebacate, diisopropyl adipate, diethyl adipate, diethyl phthalate, and a combination thereof.

In some embodiments, the bleeding preventing agent is selected from the group consisting of polyethylene glycol having an average molecular weight of 1000 to 50000, polyoxyethylene hydrogenated castor oil, stearic acid, oleic acid, sorbitan monostearate, sorbitan monooleate, sorbitan sesquioleate, sorbitan trioleate, glyceryl esters of fatty acids, and a combination thereof.

In some embodiments, the glyceryl esters of fatty acids is selected from the group consisting of glycerol monostearate 40-55 sold under the trademark Geleol™ (monoglycerides and diglycerides NF), glycerol monostearate, diglyceryl isostearate, and hexaglyceryl polyricinoleate. In some embodiments, the two or more bleeding preventing agents are polyethylene glycol having an average molecular weight of 1000 to 50000 and glyceryl esters of fatty acids. In some embodiments, the solvent is in an amount of about 50% by weight, the base is in an amount of about 4.4% by weight, the bleeding preventing agent is in an amount of about 33% by weight, and the absorption enhancer is in an amount of about 10% by weight.

In some embodiments, the topical formulation may be administered once daily, twice daily, bi-weekly, weekly, three times a week, every two weeks, every other day, monthly, every two months, every three months or as directed by a packaging or a physician to achieve the desired clinical result.

In some embodiments, the topical formulation of the embodiments herein can be manufactured according to common manufacturing methods for a topical formulation. Using an ointment as an example, an exemplary method may be as follows: first, the compound represented by the formula (I), salt thereof, or hydrate thereof, which is an active ingredient, is dissolved in a solvent by heating at 70° C. to 80° C. (Solution I). Meanwhile, an absorption enhancer and a bleeding preventing agent and other ingredients are added to the base if necessary and are dissolved by heating at 70° C. to 80° C. Then, Solution I and water, if necessary, are added to the resulting mixture, and the mixture is stirred at 70° C. to 80° C. for approximately 3 minutes. The mixing is maintained until the mixture was cooled down to approximately 32° C. (around the human skin surface temperature) and an ointment is completed. An anti-oxidizing agent may be added to the solvent if necessary.

Methods of Using the Topical Formulations

Embodiments herein are also directed to methods of treating a dermatological condition using topical formulations of embodiments herein. In some embodiments, a method of treating a dermatological condition comprises administering a topical formulation of embodiments described herein. In some embodiments, the topical formulation is topically administered. In some embodiments, the dermatological condition may be selected from dermatitis, such as, but not limited to, atopic dermatitis, seborrheic dermatitis, alopecia, contact dermatitis, psoriasis, urticaria, eczema, burns, sunburn, pancreatitis, hepatitis, lichen planus, scleritis, scleroderma, dermatomyositis, or a combination thereof. In some embodiments, the dermatological condition may be itching associated with any of the above conditions.

In some embodiments, the topical formulation used in the method of embodiments herein is a formulation disclosed in Table 1 below. In some embodiments, the topical formulation used in the method of embodiments herein is a formulation selected from Formulation C1, Formulation C2, Formulation C3 or Formulation C4 as disclosed in Table 1 below. In some embodiments the topical formulations used in the method of embodiments herein may comprise an effective amount of a compound represented by formula (I), a salt thereof, or hydrate thereof, wherein R represents hydroxyl, $C_{1-6}$ alkoxy optionally substituted with $C_{1-6}$ alkoxy, or amino optionally substituted with $C_{1-6}$ alkyl, a solvent, and a base, wherein the topical formulation comprises greater than about 30% by weight of a solvent. In some embodiments, the base is in an amount of about 0.001% to less than about 10% by weight of the topical formulation. In some embodiments, the compound represented by formula (I) is in an amount of about 0.001% to about 5%, about 0.001% to about 1%, about 0.001% to about 0.5%, about 0.01% to about 0.5%, about 0.05% to about 0.5%, about 0.1% to about 1%, about 0.4% to about 0.6%, about 0.3% to about 0.7%, about 0.2% to about 0.9%, about 0.1% to about 0.5%, about 0.2% to about 0.5% by weight of the topical formulation, a range between any two of these values, or any value within the foregoing ranges. In some embodiments, the compound represented by formula (I) may be in an amount of about 0.001%, about 0.01%, about 0.03%, about 0.05%, about 0.1%, about 0.2%, about 0.25%, about 0.3%, about 0.4%, about 0.5%, about 0.6%, about 0.7%, about 0.75%, about 0.8%, about 0.9%, about 1.0%, about 3.0%, or about 5°% by weight, or a range of any two of these values. In some embodiments, the compound represented by formula (I) is in an amount of about 0.2%. In some embodiments, the compound represented by formula (I) is in an amount of about 0.5%.

In some embodiments, the topical formulation further comprises an absorption enhancer, a bleeding preventing agent, water, or a combination thereof. In some embodiments, the topical formulation may further comprise a coloring agent, a flavoring agent, a preservative, an antioxidant, a stabilizer, pharmaceutically acceptable excipient, a usability improving agent, or a combination thereof.

In some embodiments, the bleeding preventing agent is two or more bleeding preventing agents. In some embodiments, a total amount of the bleeding preventing agent is greater than about 40% by weight of the topical formulation. In some embodiments, the absorption enhancer is in an amount of about 5% to about 20% by weight of the topical formulation. In some embodiments, the sum of the solvent and absorption enhancer is 35% to 70% by weight of the topical formulation.

In some embodiments, the compound represented by the formula (I) is methyl N-[3-(6,7-dimethoxy-2-methylamino-quinazolin-4-yl)phenyl]terephthalamic acid (RVT-501). In some embodiments, the compound represented by the formula (I) is N-[3-(6,7-dimethoxy-2-methylaminoquinazolin-4-yl)phenyl]terephthalamic acid hydrochloride.

In some embodiments, the base is selected from the group consisting of petrolatum, paraffin, liquid paraffin, microcrystalline wax, carnauba wax, white beeswax, and a combination thereof.

In some embodiments, the solvent is selected from the group consisting of polyethylene glycol having an average molecular weight of 200 to 600, dipropylene glycol, benzyl alcohol, polyoxyethylene sorbitan fatty acid ester, diethylene glycol monoethyl ether, propylene glycol, polyoxyethylene oleyl ether, polyoxyethylene octyl phenyl ether, polyoxyethylene lauryl ether, polyoxyethylene castor oil, oleic acid, and a combination thereof.

In some embodiments, the absorption enhancer is selected from the group consisting of isopropyl myristate, ethyl myristate, octyldodecyl myristate, isopropyl palmitate, isostearyl palmitate, isopropyl isostearate, butyl stearate, ethyl oleate, decyl oleate, diisopropyl sebacate, diethyl sebacate, diisopropyl adipate, diethyl adipate, diethyl phthalate, and a combination thereof.

In some embodiments, the bleeding preventing agent is selected from the group consisting of polyethylene glycol having an average molecular weight of 1000 to 50000, polyoxyethylene hydrogenated castor oil, stearic acid, oleic acid, sorbitan monostearate, sorbitan monooleate, sorbitan sesquioleate, sorbitan trioleate, glyceryl esters of fatty acids, and a combination thereof.

In some embodiments, the glyceryl esters of fatty acids is selected from the group consisting of glycerol monostearate 40-55 sold under the trademark Geleol™ (monoglycerides and diglycerides NF), glycerol monostearate, diglyceryl isostearate, and hexaglyceryl polyricinoleate. In some embodiments, the two or more bleeding preventing agents are polyethylene glycol having an average molecular weight of 1000 to 50000 and glyceryl esters of fatty acids. In some embodiments, the solvent is in an amount of about 50% by weight, the base is in an amount of about 4.4% by weight, the bleeding preventing agent is in an amount of about 33% by weight, and the absorption enhancer is in an amount of about 10% by weight.

The amount of the compound of formula (I) to be administered is that amount which is therapeutically effective. The dosage to be administered will depend on the characteristics of the subject being treated, e.g., the particular animal treated, age, weight, health, types of concurrent treatment, if any, and frequency of treatments, and can be easily determined by one of skill in the art (e.g., by the clinician).

It must also be noted that as used herein and in the appended claims, the singular forms "a," "an," and "the" include plural reference unless the context clearly dictates otherwise. Thus, for example, reference to a "bleeding preventing agent" is a reference to one or more bleeding preventing agents and equivalents thereof known to those skilled in the art, and so forth.

As used herein, the term "about" means plus or minus 10% of the numerical value of the number with which it is being used. Therefore, about 50% means in the range of 45%-55%.

"Administering" when used in conjunction with a therapeutic means to administer a therapeutic directly into or onto a target tissue or to administer a therapeutic to a patient whereby the therapeutic positively impacts the tissue to which it is targeted. Thus, as used herein, the term "administering", when used in conjunction with elastin digest, can include, but is not limited to, providing an elastin digest into or onto the target tissue; providing an elastin digest systemically to a patient by, e.g., intravenous injection whereby the therapeutic reaches the target tissue; providing an elastin digest in the form of the encoding sequence thereof to the target tissue (e.g., by so-called gene-therapy techniques). "Administering" a formulation may be accomplished by injection, topical administration, or by either method in combination with other known techniques. Such combination techniques include heating, radiation and ultrasound.

The term "subject" as used herein includes, but is not limited to, humans and non-human vertebrates such as wild, domestic and farm animals.

The term "improves" is used to convey that the present invention changes either the appearance, form, characteristics and/or the physical attributes of the tissue to which it is being provided, applied or administered. The change in form may be demonstrated by any of the following alone or in combination: enhanced appearance of the skin; decrease in symptoms of the disease.

The term "inhibiting" includes the administration of a compound of the present invention to prevent the onset of the symptoms, alleviating the symptoms, or eliminating the disease, condition or disorder.

By "pharmaceutically acceptable", it is meant the carrier, diluent or excipient must be compatible with the other ingredients of the formulation and not deleterious to the recipient thereof. The choice of pharmaceutically acceptable carrier, diluent or excipient may be determined by its suitability for the treatment regimen of the disease or medical condition concerned and reference can be made to standard reference works such as *Goodman & Gilman's The Pharmacological Basis of Therapeutics*. 11th ed. New York: McGraw-Hill; 2005, which is hereby incorporated by reference in its entirety.

Unless otherwise indicated, the term "skin" means that outer integument or covering of the body, consisting of the dermis and the epidermis and resting upon subcutaneous tissue.

As used herein, the term "therapeutic" means an agent utilized to treat, combat, ameliorate, prevent or improve an unwanted condition or disease of a patient. In part, embodiments of the present invention are directed to the treatment of cancer or the decrease in proliferation of cells.

A "therapeutically effective amount" or "effective amount" of a composition is a predetermined amount calculated to achieve the desired effect, i.e., to inhibit, block, or reverse the activation, migration, or proliferation of cells. The activity contemplated by the present methods includes both medical therapeutic and/or prophylactic treatment, as appropriate. The specific dose of a compound administered according to this invention to obtain therapeutic and/or prophylactic effects will, of course, be determined by the particular circumstances surrounding the case, including, for example, the compound administered, the route of administration, and the condition being treated. The compounds are effective over a wide dosage range and, for example, dosages per day will normally fall within the range of from 0.001 to 10 mg/kg, more usually in the range of from 0.01 to 1 mg/kg. However, it will be understood that the effective amount administered will be determined by the physician in the light of the relevant circumstances including the condition to be treated, the choice of compound to be administered, and the chosen route of administration, and therefore the above dosage ranges are not intended to limit the scope of the invention in any way. A therapeutically effective amount of compound of this invention is typically an amount such that when it is administered in a physiologically tolerable excipient composition, it is sufficient to achieve an effective systemic concentration or local concentration in the tissue.

The terms "treat," "treated," or "treating" as used herein refers to both therapeutic treatment and prophylactic or preventative measures, wherein the object is to prevent or slow down (lessen) an undesired physiological condition, disorder or disease, or to obtain beneficial or desired clinical results. For the purposes of this invention, beneficial or desired clinical results include, but are not limited to, alleviation of symptoms; diminishment of the extent of the condition, disorder or disease; stabilization (i.e., not worsening) of the state of the condition, disorder or disease; delay in onset or slowing of the progression of the condition, disorder or disease; amelioration of the condition, disorder or disease state; and remission (whether partial or total), whether detectable or undetectable, or enhancement or improvement of the condition, disorder or disease. Treatment includes eliciting a clinically significant response without excessive levels of side effects. Treatment also includes prolonging survival as compared to expected survival if not receiving treatment.

This invention and embodiments illustrating the method and materials used may be further understood by reference to the following non-limiting examples.

EXAMPLE 1: Skin Penetration Study

The study was designed to evaluate the penetration of an active ingredient, methyl N-[3-(6,7-dimethoxy-2-methylaminoquinazolin-4-yl)phenyl]terephthalamic acid (RVT-501), into and across human cadaver skin from 4 formulations and 1 drug solution using the in vitro Franz finite dose model with human cadaver skin. Phosphate buffered saline; pH 7.4±0.1 was used as receiving medium. Each cell was dosed once with 10 µL/cm2 of the respective formulation using a positive displacement pipette. At pre-selected times after dose application, a 500 µL aliquot of receiving media was removed through the sampling arm of the Franz cell and replaced with an equal volume of fresh receiving medium. A glass rod was used to spread the formulation evenly covering the entire surface area of the skin. At the conclusion of the study, the cells were disassembled and the skin was carefully removed from each cell. Each skin section was washed twice with 0.5 mL of extraction solution (the receiving medium) to collect un-absorbed formulation from the surface of the skin. The skin was carefully separated into epidermis and dermis using forceps. To each epidermis and dermis vial, homogenization solution (phosphate buffered saline, pH 7.4) was added. Tissues were homogenized using a bead homogenizer (OMNI Bead Ruptor 24.)

TABLE 1

FORMULATIONS

| Ingredients | Formulations | | | | |
|---|---|---|---|---|---|
| | B | C1 | C2 | C3 | C4 |
| Strength (%) | 0.2 | 0.2 | 0.5 | 0.2 | 0.9 |
| Active Ingredient | 0.2 | 0.2 | 0.5 | 0.2 | 0.9 |
| PEG 400 | 20 | 50.3 | 50 | 55 | 99.0 |
| PEG 4000 | 10 | 25 | 25 | 20 | — |
| Water | 2 | 2 | 2 | 2 | — |
| glycerol monostearate | 8 | 8* | 8* | 8* | — |
| White Petrolatum | 49.7 | 4.7 | 4.4 | 4.7 | — |
| Vitamin E | 0.1 | 0.1 | 0.1 | 0.1 | 0.1 |
| Isopropyl Myristate | 10 | 10 | 10 | 10 | — |
| Total | 100 | 100 | 100 | 100 | 100 |

*Glycerol monostearate, mono and diglycerides, NF sold under the tradename Geleol™ is the glycerol monostearate used in formulations C1, C2 and C3.

Figure 2:
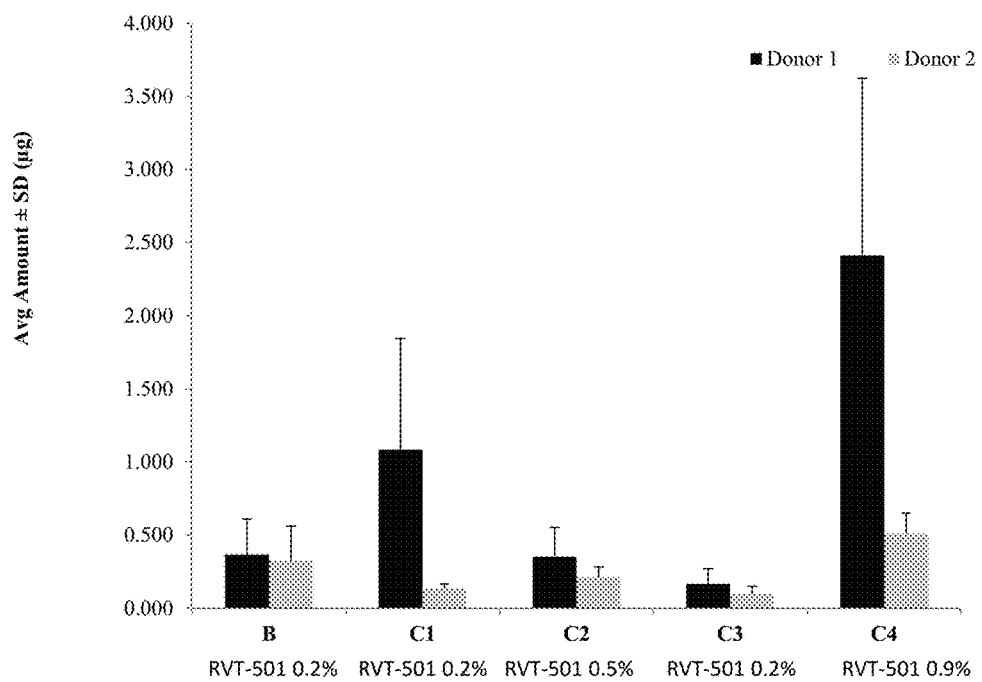
FIG. 2 illustrates the mean amount (μg) of a compound of formula (I) of embodiments herein collected from the epidermis for each donor 24 hours after application of the topical formulation of embodiments herein.
Figure 3:
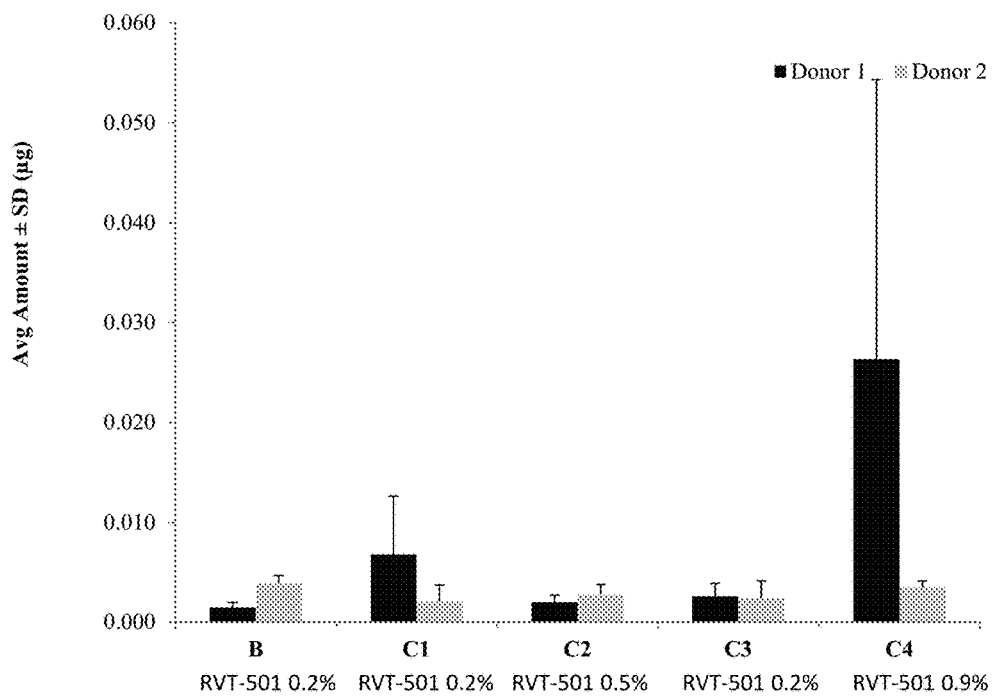
FIG. 3 illustrates the mean amount (μg) of a compound of formula (I) of embodiments herein collected from the dermis for each donor 24 hours after application of the topical formulation of embodiments herein.

The objective of this study was to evaluate the penetration of methyl N-[3-(6,7-dimethoxy-2-methylaminoquinazolin-4-yl)phenyl]terephthalamic acid (RVT-501) into and across human cadaver skin from 4 formulations (B, C1, C2, and C3) and 1 drug solution (C4). The results indicated greatest permeation of methyl N-[3-(6,7-dimethoxy-2-methylaminoquinazolin-4-yl)phenyl]terephthalamic acid (RVT-501) from the PEG-400 solution (C4). This was expected since C4 was used as a positive control in the study. Drug levels were below the limit of quantification in receptor media at 24 hours for all formulations tested. Results from donor 1 suggested C1 to have higher permeation compared to B, C2, and C3. However, donor 2 results suggested the three formulations to have nearly equivalent permeation. Overall, donor 1 showed a trend of higher permeation compared to donor 2. It was noted that donor 1 appeared visually thinner than donor 2. In addition, a dose response was not observed between the two strengths, 0.2% and 0.5%. Since a similar trend of C1 having greater permeation was not observed in both donors, it can be concluded that formulations B, C1, C2, and C3 had nearly equivalent permeation into the stratum corneum (FIG. 1), epidermis (FIG. 2), and dermis (FIG. 3).

EXAMPLE 2: Treatment of Atopic Dermatitis

Atopic dermatitis (AD) was induced in specific pathogen-free (SPF) female NC/Nga mice (n=8/group), 8-12 weeks old, by repeated percutaneous applications of dinitrochlorobenzene (DNCB) to the dorsal skin of the ears and back on days 4, 7, 10, and 13. NC/Nga mice are an established mouse model for atopic dermatitis. See Suto et al. *NC/Nga mice: a mouse model for atopic dermatitis*; Int Arch Allergy Immunol. 1999; 120 Suppl 1:70-5; and Gao et al., *Establishment of allergic dermatitis in NC/Nga mice as a model for severe atopic dermatitis*, Biol. Pharm. Bull. 2004 September; 27(9): 1376-81.

A prophylactic study and a therapeutic study was conducted:

1. Prophylactic study: 0.2% formulation (C1), 0.5% formulation (C2), RVT-501 placebo, tacrolimus placebo, 0.1% tacrolimus, or no treatment (AD control) on days 1-14 or sham-induction of AD.

Figure 4:
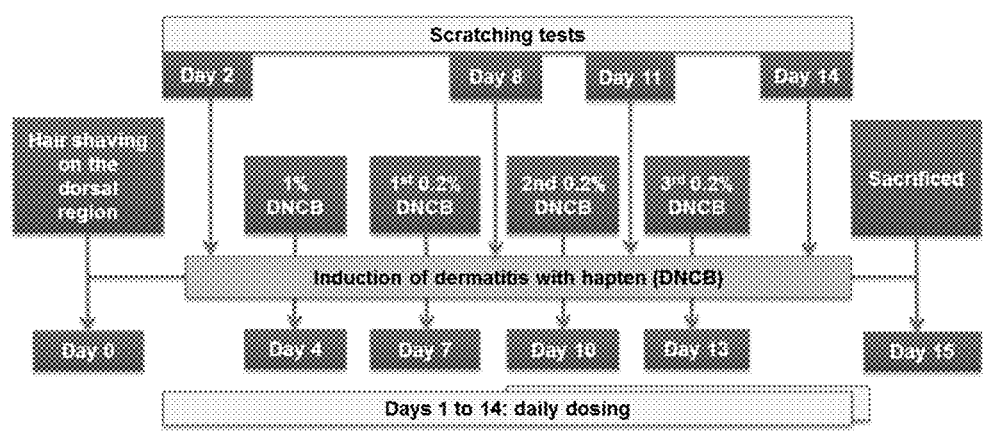
FIG. 4 illustrates the timeline of the protocol used in Example 2.

2. Therapeutic study: 0.2% formulation (C1), 0.5% formulation (C2), active ingredient placebo, tacrolimus placebo, 0.1% tacrolimus, or no treatment (AD control) on days 8-14. See FIG. 4.

Figure 5:
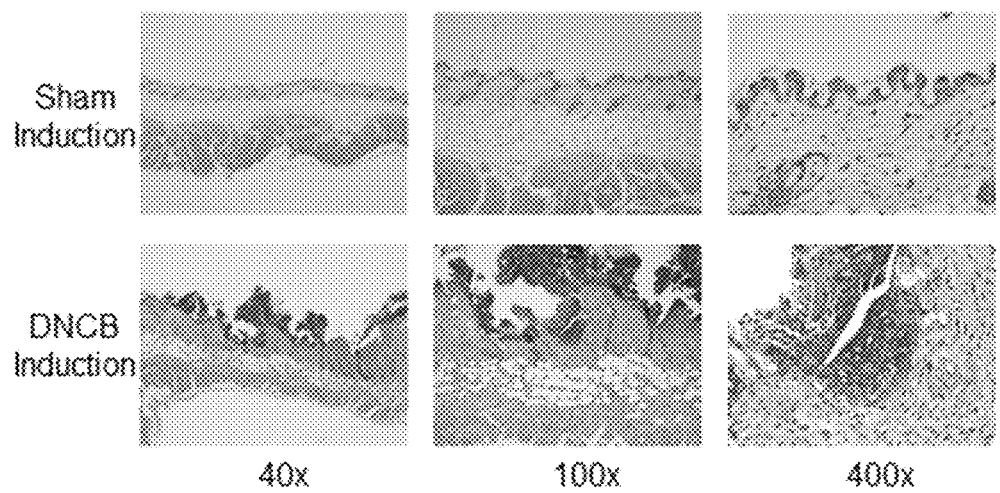
FIG. 5 illustrates hematoxylin and eosin staining of normal skin versus skin with atopic dermatitis lesions. Note the epidermal hyperplasia, hyperkeratosis, ulceration, and immune cell infiltration in the DNCB-induced skin.

Scratching assays were performed on days 2, 8, 11, 14 in both studies. Skin samples were harvested for histopathology and cytokine analysis on day 15. Histopathology of sham-induced versus DNCB-induced mouse skin indicates clear presence of atopic dermatitis. See FIG. 5.

Figure 6:
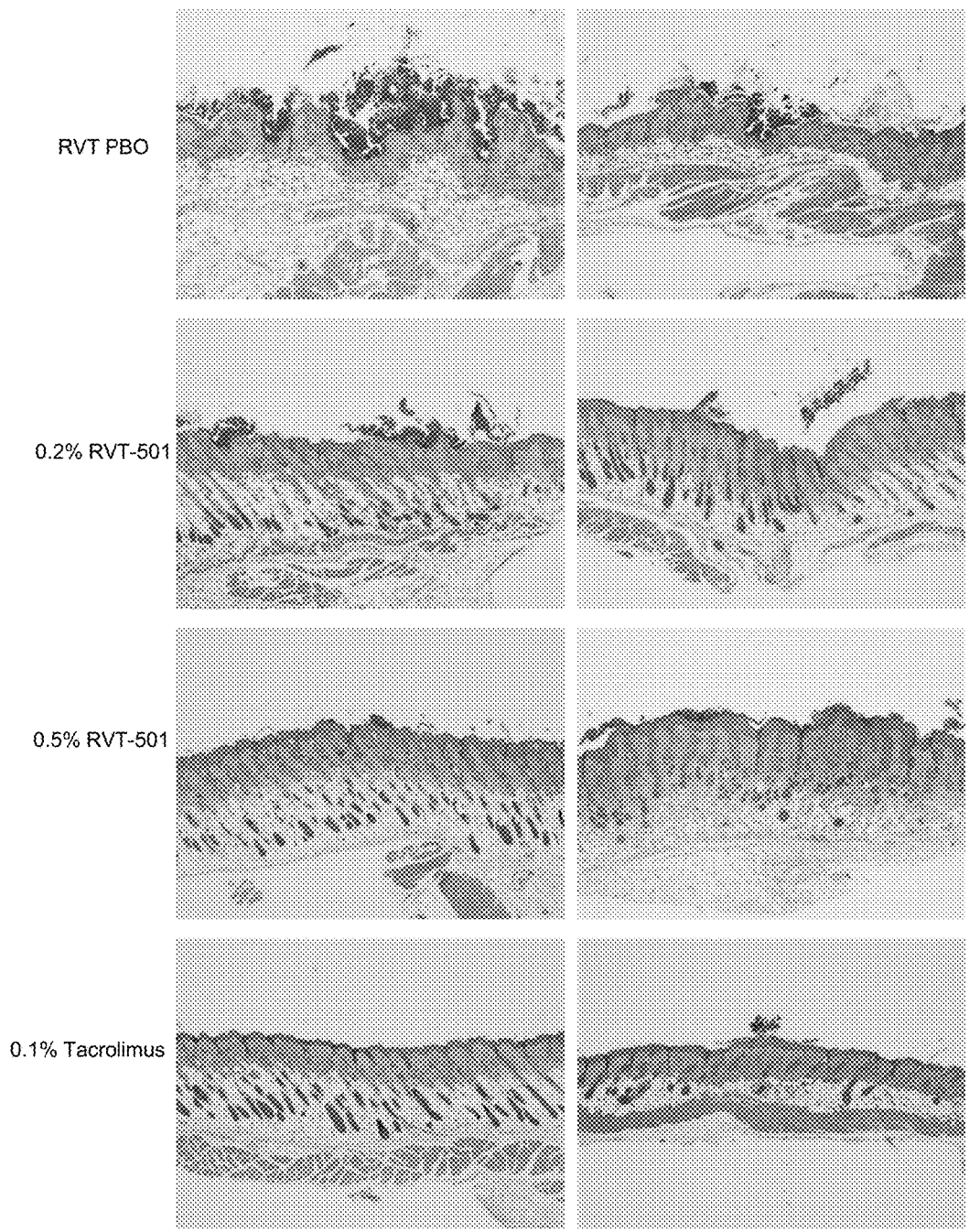
FIG. 6 illustrates hematoxylin and eosin staining of skin sections treated for atopic dermatitis skin lesions prophylactically (left) or therapeutically (right) at 40× magnification.

Skin sections were examined at day 15 for AD-associated pathology. Prophylactic treatment with 0.5% formulation (C2) or 0.1% tacrolimus attenuated AD lesions induced by DNCB at the microscopic level. See FIG. 6, left column. As a therapeutic treatment, 0.5% formulation (C2) and 0.1% tacrolimus trended toward a reduction in AD lesion severity. See FIG. 6, right column.

Figure 7:
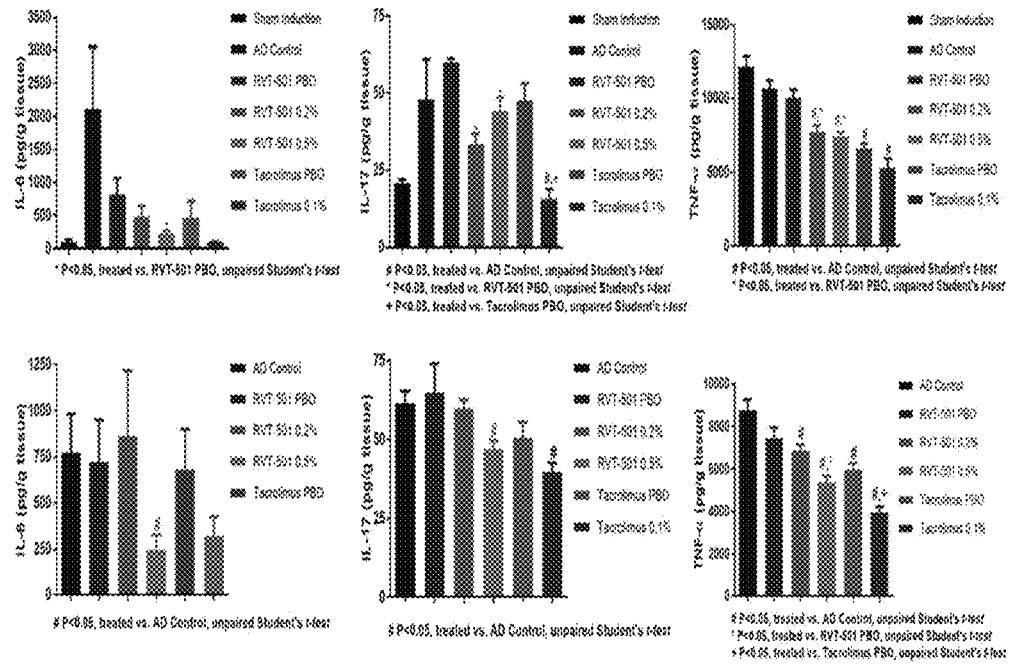
FIG. 7 illustrates select cytokine data from prophylactic (top) and therapeutic (bottom) studies. Featured cytokines are IL-6 (left), IL-17 (middle), and TNF-α (right). Data was collected from skin samples at day 15 in each study and run in a LUMINEX panel.

Skin sections were harvested for cytokine analysis at the end of each study to interrogate how these immune modulators were affected by the different treatments. Prophylactic administration of methyl N-[3-(6,7-dimethoxy-2-methylaminoquinazolin-4-yl)phenyl]terephthalamic acid (RVT-501) significantly reduced G-CSF, GM-CSF, KC, MIP-1α, and TNF-α in a dose-dependent manner. Additionally, the 0.5% formulation (C2) decreased IL-3, IL-6, IL-17, MCP-1, and MIP-1β. Therapeutically, Il-1β showed a significant dose-dependent decrease with methyl N-[3-(6,7-dimethoxy-2-methylaminoquinazolin-4-yl)phenyl]terephthalamic acid (RVT-501) treatment. Significant decreases with the 0.5% formulation (C2) were also seen with IL-3, eotaxin, G-CSF, GM-CSF, KC, MIP-1α, MIP-1β, and TNF-α. As a therapeutic, 0.1% tacrolimus significantly decreased IL-1α, IL-1β, IL-4, IL-5, IL-10, IL-12(p40), IL-13, eotaxin, GM-CSF, KC, MCP-1, MIP-1α, MIP-1β, RANTES, and TNF-α. Reduction of these inflammatory cytokines and chemokines likely contributes to the reduction in immune cell infiltration as seen via histopathology in both studies with 0.5% formulation (C2) and 0.1% tacrolimus. See FIG. 7.

Figure 8:
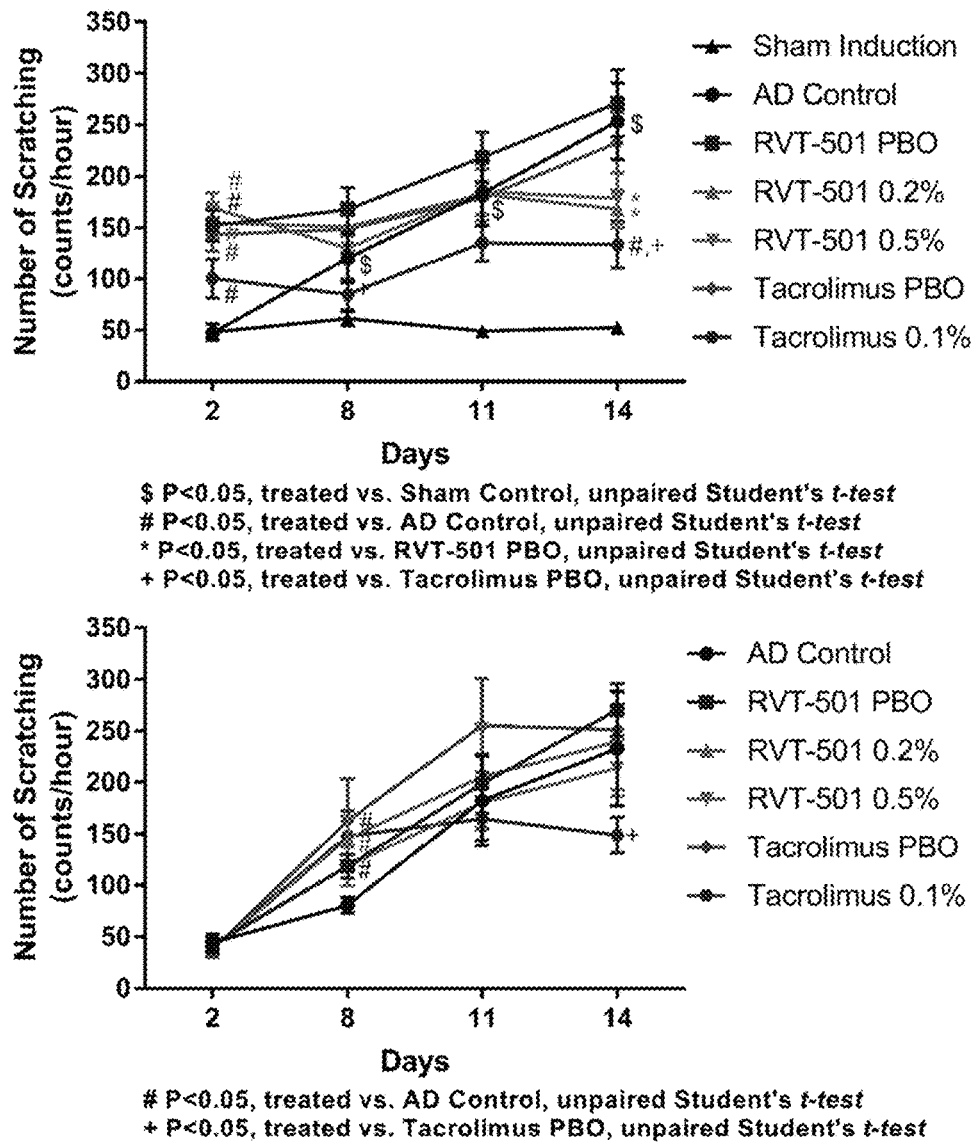
FIG. 8 illustrates scratching assay results in a prophylactic (top) and therapeutic (bottom) study.

All treatments groups show a significant reduction in scratching relative to placebo in the prophylactic study. As a therapeutic, 0.1% tacrolimus showed a significant decrease in scratching at day 14. See FIG. 8.

CONCLUSIONS: The prophylactic study showed that RVT-501 0.5% formulation (C2) significantly reduced skin ulceration and preserved skin architecture when compared to active ingredient placebo controls and AD control animals. RVT-501 0.5% formulation (C2) also significantly reduced D14 scratching events, ear thickness, AD skin lesion score, and multiple AD-related pro-inflammatory cytokines when compared to the RVT-501 placebo; all of which appeared to reflect dose dependent responses from the 0.2% to 0.5% formulations (C1 and C2, respectively). The therapeutic study showed significant reduction in AD skin lesion score versus the active ingredient placebo that appeared dose dependent, as well as trends in decreased ulceration and ear thickness with RVT-501 0.5% formulation (C2), though these latter changes did not reach statistical significance. Therapeutic treatment of the established mouse AD lesions also revealed significant decreases in AD-related pro-inflammatory cytokines, though these effects were not as prominent as the 14 day prophylactic treatment.

In summary, significant reductions in scratching, microscopic skin histopathology, and inflammatory cytokines were observed with the RVT-501 0.5% formulation (C2) and 0.1% tacrolimus administered prophylactically. Trends toward significance were seen with RVT-501 0.5% formulation (C2) administered therapeutically, and may have been achieved in a model where longer treatment is possible. Accordingly, topical methyl N-[3-(6,7-dimethoxy-2-methylaminoquinazolin-4-yl)phenyl]terephthalamic acid (RVT-501) appears to be an effective treatment for atopic dermatitis.

Although the present invention has been described in considerable detail with reference to certain preferred embodiments thereof, other versions are possible. Therefore, the spirit and scope of the appended claims should not be limited to the description and the preferred versions contained within this specification.

The invention claimed is:
1. A topical formulation comprising an effective amount of a compound represented by the formula (I), a salt thereof, or hydrate thereof,

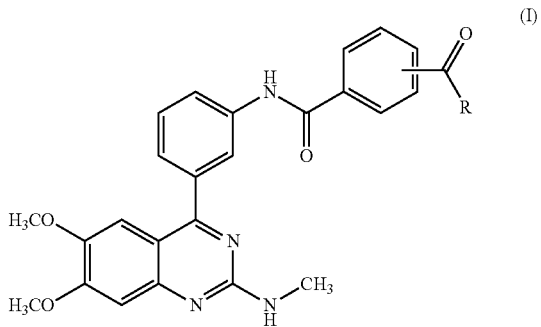

wherein R represents hydroxyl, C1-6 alkoxy optionally substituted with C1-6 alkoxy, or amino optionally substituted with C1-6 alkyl,
a bleeding preventing agent, a solvent, and a base;
wherein the topical formulation comprises about 30% to about 60% by weight of a solvent.
2. The topical formulation of claim 1, wherein the base is in an amount of about 0.001% to less than about 10% by weight of the topical formulation.
3. The topical formulation of claim 1, wherein the compound represented by formula (I) is in an amount of about 0.2% to about 0.9% by weight of the topical formulation.
4. The topical formulation of claim 1, wherein the compound represented by formula (I) is in an amount of about 0.5% by weight of the topical formulation.
5. The topical formulation of claim 1, further comprising an absorption enhancer, water, or a combination thereof.
6. The topical formulation of claim 1, wherein the bleeding preventing agent is two or more bleeding preventing agents.
7. The topical formulation of claim 1, wherein a total amount of the bleeding preventing agent is greater than about 40% by weight of the topical formulation.
8. The topical formulation of claim 5, wherein the absorption enhancer is in an amount of about 5% to about 20% by weight of the topical formulation.
9. The topical formulation of claim 5, wherein the sum of the solvent and absorption enhancer is about 35% to about 70% by weight of the topical formulation.
10. The topical formulation of claim 1, wherein the base is selected from the group consisting of petrolatum, paraffin, liquid paraffin, microcrystalline wax, carnauba wax, white beeswax, and any combination thereof.
11. The topical formulation of claim 1, wherein the solvent is selected from the group consisting of polyethylene glycol having an average molecular weight of about 200 to about 600, dipropylene glycol, benzyl alcohol, polyoxyethylene sorbitan fatty acid ester, diethylene glycol monoethyl ether, propylene glycol, polyoxyethylene oleyl ether, polyoxyethylene octyl phenyl ether, polyoxyethylene lauryl ether, polyoxyethylene castor oil, oleic acid, and any combination thereof.
12. The topical formulation of claim 1, wherein the solvent is polyethylene glycol having an average molecular weight of about 200 to about 600.
13. The topical formulation of claim 1, wherein the solvent is polyethylene glycol having an average molecular weight of about 400.
14. The topical formulation of claim 5, wherein the absorption enhancer is selected from the group consisting of isopropyl myristate, ethyl myristate, octyldodecyl myristate, isopropyl palmitate, isostearyl palmitate, isopropyl isostearate, butyl stearate, ethyl oleate, decyl oleate, diisopropyl sebacate, diethyl sebacate, diisopropyl adipate, diethyl adipate, diethyl phthalate, and any combination thereof.
15. The topical formulation of claim 1, wherein the bleeding preventing agent is selected from the group consisting of polyethylene glycol having an average molecular weight of 1000 to 50000, polyoxyethylene hydrogenated castor oil, stearic acid, oleic acid, sorbitan monostearate, sorbitan monooleate, sorbitan sesquioleate, sorbitan trioleate, glycerol esters of fatty acids, and any combination thereof.
16. The topical formulation of claim 1, wherein the bleeding preventing agent is polyethylene glycol with an average molecular weight of about 3600 to about 4400.
17. The topical formulation of claim 1, wherein the bleeding preventing agent is polyethylene glycol with an average molecular weight of about 4000.
18. The topical formulation of claim 15, wherein the glycerol esters of fatty acids is selected from the group consisting of glycerol monostearate 40-55, monoglycerides, diglycerides, monoglycerol stearates, diglycerol stearates, triglycerol stearates, diglyceryl isostearate, hexaglyceryl polyricinoleate, and any combination thereof.
19. The topical formulation of claim 6, wherein the two or more bleeding preventing agents are polyethylene glycol having an average molecular weight of 1000 to 50000 and glycerol esters of fatty acids.
20. The topical formulation of claim 1, wherein the solvent is in an amount of about 50% by weight, the base is in an amount of about 4.4% by weight, the bleeding preventing agent is in an amount of about 33% by weight, and the topical formulation further comprises an absorption enhancer in an amount of about 10% by weight.
21. The topical formulation of claim 1, wherein the compound represented by the formula (I) is:

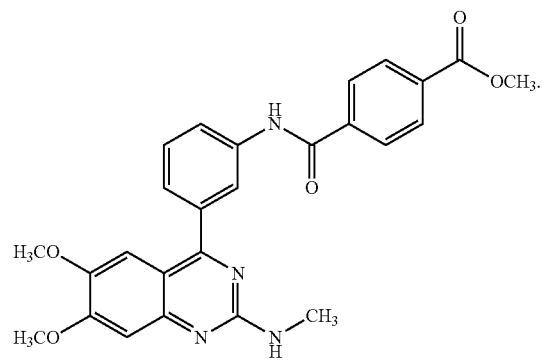 [SMILES: CNc1nc(-c2cccc(NC(=O)c3ccc(C(=O)OC)cc3)c2)c2cc(OC)c(OC)cc2n1]

22. The topical formulation of claim 21, wherein the base is in an amount of about 0.001% to less than about 10% by weight of the topical formulation.

23. The topical formulation of claim 21, wherein the compound represented by formula (I) is in an amount of about 0.2% to about 0.9% by weight of the topical formulation.

24. The topical formulation of claim 21, wherein the compound represented by formula (I) is in an amount of about 0.5% by weight of the topical formulation.

25. The topical formulation of claim 21, further comprising an absorption enhancer, water, or a combination thereof.

26. The topical formulation of claim 21, wherein the bleeding preventing agent is two or more bleeding preventing agents.

27. The topical formulation of claim 21, wherein a total amount of the bleeding preventing agent is greater than about 40% by weight of the topical formulation.

28. The topical formulation of claim 25, wherein the absorption enhancer is in an amount of about 5% to about 20% by weight of the topical formulation.

29. The topical formulation of claim 25, wherein the sum of the solvent and absorption enhancer is about 35% to about 70% by weight of the topical formulation.

30. The topical formulation of claim 21, wherein the base is selected from the group consisting of petrolatum, paraffin, liquid paraffin, microcrystalline wax, carnauba wax, white beeswax, and any combination thereof.

31. The topical formulation of claim 21, wherein the solvent is selected from the group consisting of polyethylene glycol having an average molecular weight of about 200 to about 600, dipropylene glycol, benzyl alcohol, polyoxyethylene sorbitan fatty acid ester, diethylene glycol monoethyl ether, propylene glycol, polyoxyethylene oleyl ether, polyoxyethylene octyl phenyl ether, polyoxyethylene lauryl ether, polyoxyethylene castor oil, oleic acid, and any combination thereof.

32. The topical formulation of claim 21, wherein the solvent is polyethylene glycol having an average molecular weight of about 200 to about 600.

33. The topical formulation of claim 21, wherein the solvent is polyethylene glycol having an average molecular weight of about 400.

34. The topical formulation of claim 25, wherein the absorption enhancer is selected from the group consisting of isopropyl myristate, ethyl myristate, octyldodecyl myristate, isopropyl palmitate, isostearyl palmitate, isopropyl isostearate, butyl stearate, ethyl oleate, decyl oleate, diisopropyl sebacate, diethyl sebacate, diisopropyl adipate, diethyl adipate, diethyl phthalate, and any combination thereof.

35. The topical formulation of claim 21, wherein the bleeding preventing agent is selected from the group consisting of polyethylene glycol having an average molecular weight of 1000 to 50000, polyoxyethylene hydrogenated castor oil, stearic acid, oleic acid, sorbitan monostearate, sorbitan monooleate, sorbitan sesquioleate, sorbitan trioleate, glycerol esters of fatty acids, and any combination thereof.

36. The topical formulation of claim 21, wherein the bleeding preventing agent is polyethylene glycol with an average molecular weight of about 3600 to about 4400.

37. The topical formulation of claim 21, wherein the bleeding preventing agent is polyethylene glycol with an average molecular weight of about 4000.

38. The topical formulation of claim 35, wherein the glycerol esters of fatty acids is selected from the group consisting of glycerol monostearate 40-55, monoglycerides, diglycerides, monoglycerol stearates, diglycerol stearates, triglycerol stearates, diglyceryl isostearate, hexaglyceryl polyricinoleate, and any combination thereof.

39. The topical formulation of claim 26, wherein the two or more bleeding preventing agents are polyethylene glycol having an average molecular weight of 1000 to 50000 and glycerol esters of fatty acids.

40. The topical formulation of claim 21, wherein the solvent is in an amount of about 50% by weight, the base is in an amount of about 4.4% by weight, the bleeding preventing agent is in an amount of about 33% by weight, and the topical formulation further comprises an absorption enhancer in an amount of about 10% by weight.

* * * * *